US00PP19906P2

(12) United States Plant Patent
Huang

(10) Patent No.: US PP19,906 P2
(45) Date of Patent: Apr. 14, 2009

(54) ***PHALAENOPSIS* PLANT NAMED 'QUEEN V6'**

(50) Latin Name: ***Phalaenopsis* sp.**
Varietal Denomination: Queen V6

(75) Inventor: Tsung-Te Huang, Xinying (TW)

(73) Assignee: Tai-Ling Biotech Inc., Tainan County (TW)

( * ) Notice: Subject to any disclaimer, the term of this patent is extended or adjusted under 35 U.S.C. 154(b) by 0 days.

(21) Appl. No.: 11/980,505

(22) Filed: Oct. 31, 2007

(51) Int. Cl.
*A01H 5/00* (2006.01)

(52) U.S. Cl. ..... Plt./311
(58) Field of Classification Search ..... Plt./311
See application file for complete search history.

*Primary Examiner*—Annette H Para
(74) *Attorney, Agent, or Firm*—Muncy, Geissler, Olds & Lowe, PLLC

(57) ABSTRACT

A new and distinct cultivar of *Phalaenopsis* plant named 'Queen V6', having big orbicular, flowers with yellow light-colored labellum; upright and sturdy flowering stems, and excellent postproduction longevity.

2 Drawing Sheets

Botanical classification: *Phalaenopsis* sp.
Variety denomination: 'Queen V6'.

The present invention relates to botanical classification/cultivar designation: *Phalaenopsis* Orchid cultivar Queen V6.

BACKGROUND OF THE INVENTION

The present invention comprises a new and distinct cultivar of *Phalaenopsis* Orchid, and hereinafter referred to by the cultivar name, 'Queen V6'.

The new cultivar is a planned breeding program conducted by the inventor in Tainan, Taiwan. The objective of the breeding program is to create new uniform pot-type *Phalaenopsis* Orchid cultivars having attractive flower coloration.

The new cultivar was discovered by the inventor from within the progeny of a cross-pollination of two unidentified proprietary selections of *Phalaenopsis* Orchids, not patented, on Dec. 16, 1999, in a controlled environment in Tainan, Taiwan.

Asexual propagation by tissue culture in a laboratory in Tainan, Taiwan has been used to increase the number of plants for evaluation and has demonstrated that the unique combination of characteristics as herein disclosed for the new *Phalaenopsis* Orchid, 'Queen V6,' are retained through successive generations of asexual reproduction.

SUMMARY OF THE INVENTION

The following traits have been repeatedly observed and are determined to be basic characteristics of new cultivar which in combination distinguish this *Phalaenopsis* Orchid, 'Queen V6,' as a new and distinct cultivar:

1. Flowers whose width in front view is broad, about 13 to 14 cm.
2. Flowers having a persistent habit.
3. Upright and sturdy flowering stems.
4. Excellent postproduction longevity.

Plants of the new cultivar differ primarily from plants of the parent cultivar in flower shape.

Plants of the new *Phalaenopsis* Orchid can be compared to plants of the cultivar *P.* Sogo Yukidian, disclosed in RHS. In side-by-side comparisons conducted in Tainan, Taiwan, plants of the new *Phalaenopsis* Orchid differed from plants of the cultivar *P.* Sogo Yukidian in the following characteristics:

1. Plants of the new *Phalaenopsis* Orchid are bigger than plants of the cultivar *P.* Sogo Yukidian.
2. Plants of the new *Phalaenopsis* Orchid have broader leaves than plants of the cultivar *P.* Sogo Yukidian.
3. Plants of the new *Phalaenopsis* Orchid have shorter inflorescences than plants of the cultivar *P.* Sogo Yukidian.
4. Plants of the new *Phalaenopsis* Orchid have thinner peduncles than plants of the cultivar *P.* Sogo Yukidian.
5. Plants of the new *Phalaenopsis* Orchid have larger flowers than plants of the cultivar *P.* Sogo Yukidian.

BRIEF DESCRIPTION OF THE DRAWINGS

Colors in the photographs may appear different from the color values that appear in the detailed botanical description which accurately describe the new cultivar.

DETAILED DESCRIPTION OF THE PREFERRED EMBODIMENTS

Figure 1:
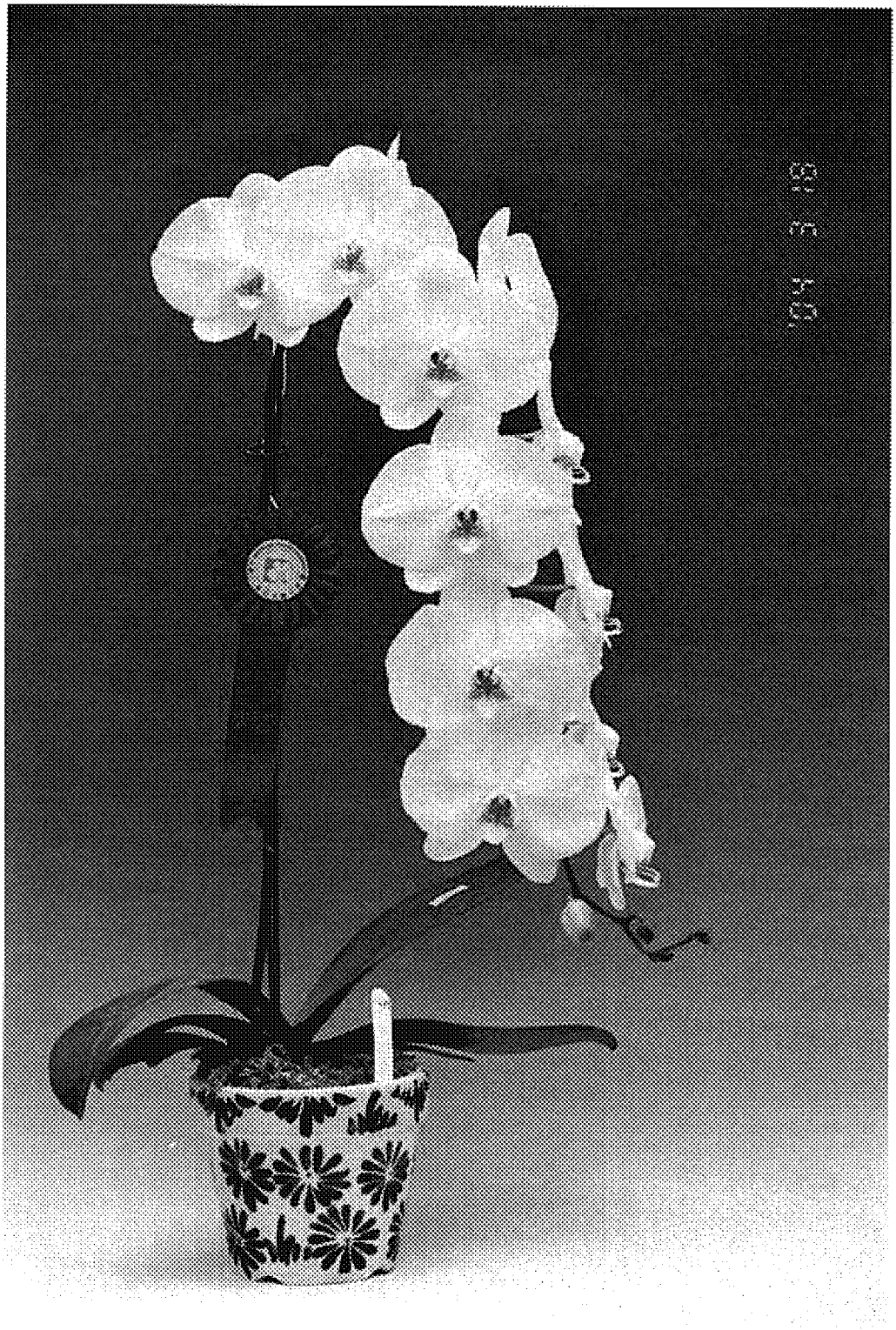
FIG. 1 is a side view of a plant of 'Queen V6' flowering in a 12 cm pot.
Figure 2:
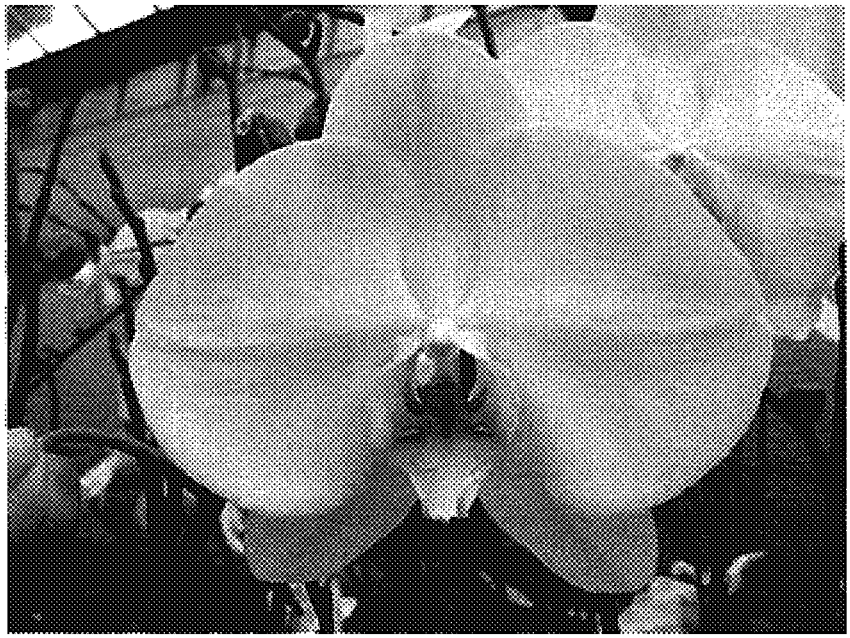
FIG. 2 is a close-up view showing the characteristics of the flower.
Figure 3:
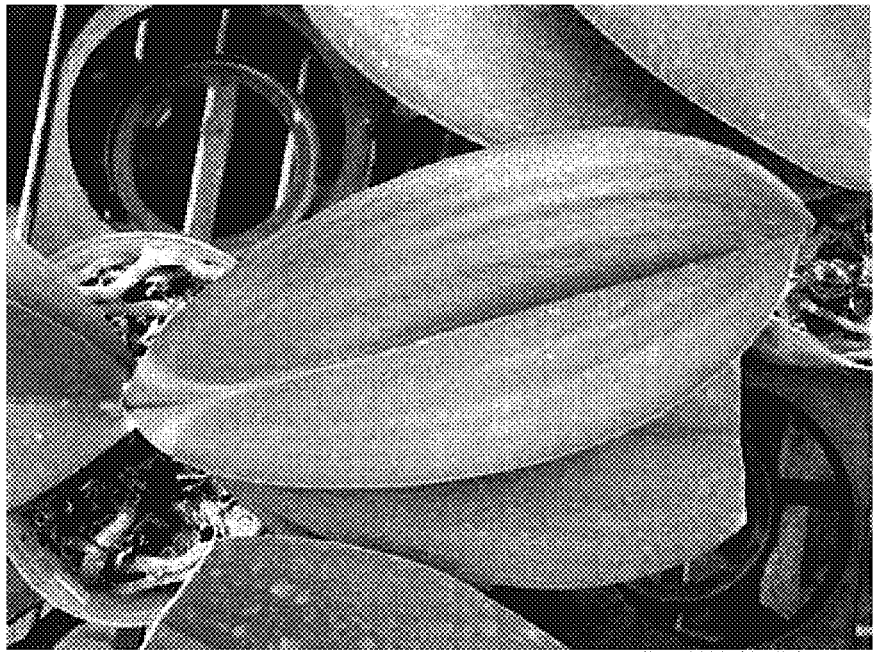
FIG. 3 is a close-up view showing the characteristics of the leaf.

Plants of the new cultivar have not been observed under all possible environmental conditions. The phenotype may vary significantly with variations in environment such as temperature and light intensity, without however, any change in genotype. In the following description, color references are made to The Royal Horticultural Society Colour Chart, except where general terms of ordinary dictionary significance are used.

Plants used for the aforementioned photographs and following detailed botanical description were grown in 12-cm containers in Tainan, Taiwan, in a greenhouse. The average temperature during vegetative growth was about 25–33° C., and the average temperature during reproductive growth was about 17–25° C.

Parentage:
- *Seed.*—Unidentified proprietary selection of *Phalaenopsis,* not patented.
- *Pollen.*—Unidentified proprietary selection of *Phalaenopsis,* not patented.
- *Propagation.*—Asexual propagation by tissue culture.

Plant description:
- *Plant shape.*—Two-ranked leaves affixed to a short central stem (monopodial growth) and inflorescences growing from leaf axils. Single flowers are arranged on upright flowering racemes.
- *Plant height, soil level to top of foliar plane.*—About 20 to 25 cm.
- *Plant height, soil level to top of inflorescences.*—About 80 to 85 cm.
- *Plant diameter.*—About 32 to 35 cm.
- *Flowers per stem.*—Approximately 55 to 60.

Foliage description:
- *Quantity per plant.*—About 6 to 7.
- *Length.*—About 18 to 19 cm.
- *Width.*—About 8 to 9 cm.
- *Shape.*—Elliptical.
- *Apex.*—Obtuse and rounded to retuse.
- *Base.*—Cuneate.
- *Margin.*—Entire.
- *Aspect.*—Mostly flat and folded upward from the midrib.
- *Texture, upper and lower surfaces.*—Leathery, thick, glabrous, with the texture of the upper surface being more obvious than the texture of the lower surface.
- *Venation.*—Parallel; midrib veins are sunken within the lamina.
- *Color* (*upper surface*).—Closest to RHS 137C.
- *Color* (*lower surface*).—Closest to RHS 143C.

Flower description:
- *Flower type.*—Single zygomorphic flowers, roughly elliptical in shape.
- *Flower arrangement.*—Racemes.
- *Flowering stems.*—Upright.
- *Flowering habit.*—Plants typically produce one to two branched flowering stems at least 10 to 12 flowers each.
- *Fragrance.*—Flowers are not fragrant.
- *Self cleaning or persistent.*—Flowers persistent.
- *Natural flowering season.*—From January to April in southern Taiwan.
- *Post-production longevity.*—Plants of 'Queen V6' maintain good leaf and flower substance for about three to five months on the plant under interior environmental conditions.
- *Inflorescence length.*—About 80 to 85 cm.
- *Inflorescence diameter.*—About 35 to 42 cm.
- *Flower width in front view.*—About 12 to 13 cm.
- *Flower length in front view.*—About 9 cm.

Petals:
- *Quantity.*—Two per flower.
- *Length.*—About 8 cm.
- *Diameter.*—About 6 cm.
- *Shape.*—Broadly ovate.
- *Apex.*—Rounded.
- *Base.*—Attenuate; fused with the column.
- *Margin.*—Entire.
- *Texture, upper and lower surfaces.*—Velvety.
- *Color.*—The main color of both the adaxial and abaxial surfaces of the petal is white (RHS N155A).

Labellum:
- *Width, not flattened.*—About 2.5 cm.
- *Length, not flattened.*—About 3 cm.
- *Callosites.*—Present.
- *Shape.*—Deeply three-lobed with two prominent callosities on the upper surface at the central junction of the lateral lobed and base of midlobe.
- *Base color of the abaxial surface of the apical lobe.*—RHS 172B.
- *Tip color of the adaxial surface of the apical lobe.*—RHS 159D.

Sepals:
- *Quantity.*—Two per flower.
- *Length.*—About 6 cm.
- *Diameter.*—About 4.7 cm.
- *Shape.*—Elliptic to ovate.
- *Apex.*—Rounded.
- *Base.*—Attenuate; fused with the petals and column.
- *Margin.*—Entire.
- *Texture, upper and lower surfaces.*—Velvety.
- *Dorsal sepal color.*—RHS N80C.
- *Lateral sepal color.*—RHS N80C.
- *Lateral sepal pattern color.*—RHS N80C.

Peduncles:
- *Length.*—About 55 to 58 cm.
- *Diameter.*—About 5 mm.
- *Aspect.*—Upright.
- *Strength.*—Strong.
- *Texture.*—Smooth, glabrous.
- *Color.*—RHS 148A.

Pedicels:
- *Length.*—About 3 cm.
- *Length.*—About 8 mm.
- *Aspect.*—About 80° from vertical.
- *Strength.*—Strong.
- *Texture.*—Smooth, glabrous.
- *Color.*—RHS 145A.

Reproductive organs: The stamens and pistils are fused into a column, and anthers and pollen grains are united into a pollinia. The stigma is situated under the column and behind the pollinia.

Column:
- *Length.*—About 1.1 cm.
- *Diameter.*—About 6 mm.
- *Color.*—RHS N155D.

Pollinia:
- *Quantity.*—Moderate.
- *Diameter.*—About 1.5 mm.
- *Color.*—RHS N25B.

Ovary:
- *Length.*—About 9 mm.
- *Diameter.*—About 3 mm.
- *Color.*—RHS 75B.

Root: In summer and winter, it took about 50 days at 28° C. to initiate and elongate roots. In summer, it took about 176 days at 28° C. to produce a fully rooted young plant. In winter, it took about 195 days at 28° C. to produce a fully rooted young plant.

*Diameter.*—About 5 mm.

*Color.*—146C.

Plant disease resistance/susceptibility: Resistance to known pathogens and pests common to *Phalaenopsis* Orchid has not been observed on plants of the new cultivar grown under commercial greenhouse conditions.

Temperature tolerance: Plants of the new *Phalaenopsis* Orchid have been observed to be tolerant to temperatures from about 14 to 33° C.

What is claimed is:

1. A new and distinct cultivar of *Phalaenopsis* plant named 'Queen V6', as illustrated and described.

* * * * *